United States Patent
Murthy et al.

(10) Patent No.: US 6,963,016 B1
(45) Date of Patent: Nov. 8, 2005

(54) PROCESS FOR THE SYNTHESIS OF HIGHLY ACTIVE MODIFIED CARBON SUPPORTED PALLADIUM CATALYST

(75) Inventors: Janmanchi K. Murthy, Andhra Pradesh (IN); Sridara C. Shekar, Andhra Pradesh (IN); Kamaraju S. Ramarao, Andhra Pradesh (IN); Burri D. Raju, Andhra Pradesh (IN); Kondapuram Vijaya Raghavan, Andhra Pradesh (IN)

(73) Assignee: Council of Scientific and Industrial Research, New Delhi (IN)

( * ) Notice: Subject to any disclaimer, the term of this patent is extended or adjusted under 35 U.S.C. 154(b) by 115 days.

(21) Appl. No.: 10/651,045

(22) Filed: Aug. 29, 2003

Related U.S. Application Data

(62) Division of application No. 09/983,230, filed on Oct. 23, 2001, now Pat. No. 6,624,109.

(51) Int. Cl.$^7$ ............................................. C07C 17/23

(52) U.S. Cl. .................. 570/156; 570/1; 570/123; 570/153; 570/155

(58) Field of Search ................... 570/1, 123, 153, 570/155, 156

(56) References Cited

U.S. PATENT DOCUMENTS

| | | | |
|---|---|---|---|
| 3,328,465 A | 6/1967 | Spiegler et al. | 260/580 |
| 4,361,500 A | 11/1982 | Mathe et al. | 252/430 |
| 4,835,074 A | 5/1989 | Bolster et al. | 429/43 |
| 5,110,779 A | 5/1992 | Hucul et al. | 502/185 |
| 5,326,914 A * | 7/1994 | Baker | 570/176 |
| 5,629,462 A | 5/1997 | Rao | 570/176 |
| 5,969,164 A | 10/1999 | Budge et al. | 549/508 |
| 6,368,998 B1 | 4/2002 | Lockemeyer | 502/347 |
| 2002/0137957 A1 | 9/2002 | Lockemeyer | 549/534 |
| 2002/0143197 A1 | 10/2002 | Lockemeyer | 549/534 |

FOREIGN PATENT DOCUMENTS

| | | |
|---|---|---|
| DE | 956340 C | 1/1957 |
| DE | 19720475 A | 11/1998 |
| EP | 0508660 A1 | 10/1992 |
| EP | 0669304 A1 | 5/1994 |
| NL | 9401574 | 9/1994 |

* cited by examiner

Primary Examiner—Johann Richter
Assistant Examiner—Lansana Nyalley
(74) Attorney, Agent, or Firm—Nixon & Vanderhye P.C.

(57) ABSTRACT

The present invention relates to a process for the synthesis of highly active modified carbon supported palladium catalyst by simultaneously impregnating activated carbon with a palladium precursor and an aluminium precursor. The carbon supported palladium catalyst is useful for the hydrodechlorination of dichlorodifluoromethane to produce difluoromethane.

31 Claims, No Drawings

PROCESS FOR THE SYNTHESIS OF HIGHLY ACTIVE MODIFIED CARBON SUPPORTED PALLADIUM CATALYST

This application is a Divisional of application Ser. No. 09/983,230, filed Oct. 23, 2001, now U.S. Pat. No. 6,624,109 the entire content of which is hereby incorporated by reference in this application.

FIELD OF THE INVENTION

The present invention relates to a process for the synthesis of a highly active modified carbon supported palladium catalyst. The catalyst prepared by the process of the invention is useful in the hydrodechlorination of dichlorodifluoromethane to produce difluoromethane.

BACKGROUND OF THE INVENTION

Hydrodechlorination is a process wherein removal of chlorine from chlorine containing compounds such as chloroorganics like chlorofluorocarbons (CFC's) takes place in the presence of hydrogen. Palladium catalysts are preferred for the hydrodechlorination of CFC's in gas phase. Difluoromethne (HFC-32) known as a deep refrigerant is a resultant product of the hydrodechlorination of dichlorodifluoromethane (CFC-12) over palladium based catalysts in vapour phase. Selective formation of HFC-32 by hydrodechlorination of CFC-12 depends on the nature of the catalyst used, the selection of support and the method of preparation which is the black art of the process.

Several methods are known in the art for the preparation of catalysts useful in the hydrodechlorination of CFC-12. Japanese patent application No. 339182JP 0601 731 PCT discloses a process using palladium on activated carbon as a hydrodechlorination catalyst for the production of HFC-32 with a conversion of CFC-12 of 80% and a yield of HFC-32 of 20%. WO 9617683 discloses a process for the production of HFC-32 with a selectivity of ~80% over palladium—platinum/carbon catalyst. Reference may also be made to another patent application number ENCSM, 34053 Montpellier (CA. No. 119:94820t) which discloses palladium supported on a metal oxide or metal fluoride ($Al_2O_3$ or $AlF_3$ respectively) as hydrodechlorination catalyst. The main drawback of oxide supports is the lack of resistance to HF/HCl produced during the reaction. Under this corrosive reaction atmosphere wherein HF/HCl is a by-product, the acidity of the catalyst changes and the oxide support is transformed to hydroxy/oxide fluorides or fluorides resulting in loss of activity. Fluoride supports catalyst side reactions and leads to low yield of the hydrodechlorination product. Also the preparation of fluoride supports involves corrosive reactions due to the use of HF as a reactant. A process for which a patent application has been filed by researchers of the Delft University of Technology, Netherlands reveals high CFC-12 conversion with high selectivity to HFC-32. However, this process is reportedly carried out under a pressure of 0.3–0.5 Mpa. U.S. Pat. No. 5,426,252 discloses the fast deactivation of catalyst comprising of palladium or Group IV B metal carbides. Copending Indian patent application No. 537/Del/99 and 536/Del/99 discloses a process for the use of highly active palladium supported on carbon covered alumina as a catalyst for the hydrodechlorination of CFC-12 with a conversion of 68% and HFC-32 selectivity of 70%. The main drawbacks of the above processes is that of low conversion or low selectivity to HFC-32 or severe operation conditions.

Accordingly, it is important to develop new or modified catalysts, which overcome the disadvantages of the prior art listed above.

OBJECTS OF THE INVENTION

The main object of the invention is to provide a process for the synthesis of modified highly active carbon supported palladium catalyst which is useful in the hydrodechlorination of CFC-12 to HFC-32.

It is another object of the invention to provide a method for carbon modification by metal oxides preferably Group III metal oxides such as alumina.

Yet another object of the invention is to provide a modified carbon supported palladium catalyst with low amounts of metal oxide and palladium loading on the catalyst.

A further object of the invention is to provide a catalyst for the hydrodechlorination of CFC-12 to HFC-32, which is economical and efficient.

SUMMARY OF THE INVENTION

By continuous research and experimental studies on the synthesis of good Pd based hydrodechlorination catalysts by the modification of activated carbon support by the addition of small amounts of aluminium particularly using an organic precursor along with the palladium precursor by co-impregnation technique using a suitable solvent. a good hydrodechlorination catalyst is obtained with high conversion of CFC-12 and high selectivity towards HFC-32.

Accordingly the present invention provides a process for the synthesis of highly active modified carbon supported palladium catalyst comprising simultaneously impregnating activated carbon with a palladium precursor and an aluminium precursor.

In one embodiment of the invention, the aluminium precursor used comprises an organic precursor of aluminium.

In a further embodiment of the invention, the organic aluminium precursor used comprises aluminium isopropoxide.

In another embodiment of the invention, the palladium loading percentage on the support is in the range of 2–6 wt %. preferably 4 wt %.

In yet another embodiment of the invention, the loading percentage of alumina in the support is in the range of 1–50 wt %, preferably in the range of 5–20 wt %.

In another embodiment of the invention, the co-impregnation of the support is done in the presence of tetraethyl ammonium hydroxide aqueous solution.

In a further embodiment of the invention, the conversion of CFC-12 is to the order of 85% and the selectivity to HFC-32 is to the order of 85% at atmospheric pressure.

DETAILED DESCRIPTION OF THE INVENTION

By selecting aluminium isopropoxide, an organic precursor to deposit on activated carbon, it is possible to obtain highly dispersed aluminium specie on the carbon. Co-impregnation of Pd and Al precursors on activated carbon is done to maintain an interaction between palladium and aluminium specie. This gives a scope to obtain the combined properties of Pd/C and $Pd/Al_2O_3$. The use of tetraethyl ammonium hydroxide aqueous solution during the deposition solves the solubility problem of $PdCl_2$ and aluminium isopropoxide.

The catalyst resulting from the process of the invention is prepared using commercial activated carbon as the support material. Palladium loading is maintained in the range of 2–6 wt %, preferably at 4 wt % with respect to the activated carbon. The alumina content in the catalyst is maintained in the range of 1–50 wt% preferably 5–20 wt %. with respect to the activated carbon. The prepared catalyst is reduced in $H_2$ flow prior to get reaction to obtain palladium in metallic form.

The activity of the catalyst was evaluated in an online continuous flow micro reactor (10 mm id. And 250 mm long) made of pyrex glass interfaced with a gas chromatograph equipped with TCD/FID. 1 gram of the catalyst material is placed in the center of the reactor between two plugs of quartz wool. The reactor is placed in an electrically heated furnace and the temperature of the catalyst is controlled/monitored by PID temperature programmer via a thermocouple inserted in a thermowell near to the catalyst bed. The catalyst material in the reactor is then reduced in hydrogen flow (30–80 cc/min) in a temperature range of 200–500° C. preferably in the range of 300–400° C. for a period in the range of 4–6 hours. After the reaction temperature is attained, CFC-12 feed along with $H_2$ and an inert gas such as $N_2$ to maintain the required space velocity is passed on to the catalyst bed. The product mixture coming out of the reactor is first scrubbed with an alkali taken in a trap to remove HF or HCl produced during the reaction and then passed to the gas chromatograph through a six port valve having a 0.5 ml loop. The HF/HCl free product mixture is then analysed by the gas chromatograph at regular intervals.

Prior to the deposition of palladium and aluminium precursors on the activated carbon, the support is purified by treating it with hot concentrated $HNO_3$, hot deionized water, hot ammonia solution, again hot deionized water in a sequential manner for several times in order to remove metal and other impurities. The carbon support used in this study is obtained from M/s Norit. The BET Surface area of the support was found to be 960 $m^2/g$. The support was in the form of 0.5 mm dia extrudates.

The amounts of loading of the Pd and $Al_2O_3$ are low. The catalyst demonstrated a conversion of CFC-12 and selectivity to HFC-32 to the order of 85%. The activated carbon is readily and cheaply available thereby reducing the cost of manufacture. The combined beneficial properties of both alumina and palladium and activated carbon to secure greater dispersion of alumina are an added advantage of the invention.

The invention will now be described in greater detail with reference to the following examples which are illustrative and should not be construed as limiting the scope of the invention in any manner.

EXAMPLE 1

Effect of Addition of Palladium and Aluminium Precursors:

Simultaneous and step wise impregnation of aluminium isopropoxide and palladium chloride respectively on activated carbon are adopted in examples 1(a) and 1(b).

1(a): Co-Impregnation of Aluminium and Palladium Precursors:

10 gms of activated carbon is impregnated simultaneously with aluminium isopropoxide (4.010 gms) and palladium chloride (0.68 gms) taken in 50 ml of tetraethyl ammonium hydroxide. The resultant mixture is placed on a hot plate to remove the excess solvent. The material is dried in hot air oven at 120° C. for 12 hours. The resultant catalyst is designated as Pd/ACC-1(a).

TABLE 1

Activity of Pd/ACC-1(a) catalyst GHSV = 4800/h; $H_2$/CFC-12 = 8

| Temperature ° C. | % Conversion of CFC-12 | Selectivity to HFC-32 | Selectivity to $CH_4$ | % Yield of HFC-32 |
|---|---|---|---|---|
| 180 | 23 | 96 | 4 | 22 |
| 200 | 44 | 91 | 7 | 40 |
| 220 | 61 | 91 | 7 | 56 |
| 240 | 74 | 88 | 10 | 65 |
| 250 | 82 | 87 | 10 | 72 |
| 260 | 86 | 86 | 11 | 74 |
| 280 | 96 | 65 | 32 | 62 |
| 320 | 100 | 52 | 33 | 52 |

1(b): Step Wise Impregnation of Aluminium and Palladium Precursors 10 gms of activated carbon is impregnated with aluminium isopropoxide (4.010 gms) taken in 40 ml tetraethyl ammonium hydroxide solution followed by evaporation of excess solution and then drying at 120° C. for 12 hours. 6 grams of this material is then calcined under $N_2$ flow at 450° C. for 4 hours. This calcined material (3.8 gms after calcination) is impregnated with palladium chloride (0.26 gms) taken in a 10 ml tetraethyl ammonium hydroxide solution. The excess solvent is removed by heating on a hot plate followed by drying at 120° C. for 12 hours. The resultant catalyst is designated at Pd/ACC-1(b).

TABLE 2

Activity of Pd/ACC-1(b) catalyst GHSV = 4800/h; $H_2$/CFC-12 = 8

| Temperature ° C. | % Conversion of CFC-12 | Selectivity to HFC-32 | Selectivity to $CH_4$ | % Yield of HFC-32 |
|---|---|---|---|---|
| 180 | 3 | 100 | 0 | 3 |
| 200 | 5 | 91 | 9 | 4 |
| 220 | 7 | 81 | 15 | 6 |
| 240 | 14 | 70 | 26 | 10 |
| 260 | 37 | 61 | 39 | 22 |
| 280 | 52 | 52 | 44 | 27 |
| 320 | 100 | 34 | 51 | 34 |

EXAMPLE 2

Effect of Aluminium Precursor

In order to determine the effect of aluminium precursor on the activity. three precursors, aluminum isopropoxide. aluminium nitrate and aluminium chloride respectively were used (in Example 1(a), Example 2(a) and Example 2(b) respectively). The mode of adding of Pd and Al precursors was by co-impregnation.

2(a): Aluminum Nitrate Precursor 10 gms of activated carbon is impregnated simultaneously with aluminium nitrate (7.358 gms) and palladium chloride (0.68 gms) taken in 70 ml of tetraethyl ammonium hydroxide. The mixture is placed on a hot plate to remove excess solvent. The material is dried in hot air oven at 120° C. for 12 hours. Resultant catalyst is designated Pd/ACC-2(a).

TABLE 3

Activity of Pd/ACC-2(a) catalyst GHSV = 4800/h; $H_2$/CFC-12 = 8

| Temperature °C | % Conversion of CFC-12 | Selectivity to HFC-32 | Selectivity to $CH_4$ | % Yield of HFC-32 |
|---|---|---|---|---|
| 180 | 5 | 91 | 9 | 4 |
| 200 | 7 | 85 | 15 | 6 |
| 220 | 10 | 81 | 13 | 18 |
| 240 | 13 | 87 | 13 | 12 |
| 250 | 19 | 86 | 14 | 16 |
| 260 | 26 | 81 | 17 | 21 |
| 280 | 38 | 79 | 19 | 30 |
| 320 | 63 | 75 | 21 | 47 |

2(b) Aluminium Chloride Precursor 7 gms of activated carbon is impregnated simultaneously with aluminium chloride (1.83 gms) and palladium chloride (0.478 gms) taken in 50 ml of tetraethyl ammonium hydroxide. The resultant mixture is placed on a hot plate to remove the excess solvent. The material is dried in hot air oven at 120° C. for 12 hours. The resultant catalyst is designated as Pd/ACC-1(a).

TABLE 4

Activity of Pd/ACC-2(b) catalyst GHSV = 4800/h; $H_2$/CFC-12 = 8

| Temperature °C | % Conversion of CFC-12 | Selectivity to HFC-32 | Selectivity to $CH_4$ | % Yield of HFC-32 |
|---|---|---|---|---|
| 180 | 2 | 76 | 24 | 1.5 |
| 200 | 4 | 75 | 16 | 3 |
| 220 | 7 | 64 | 29 | 4.5 |
| 240 | 14 | 69 | 27 | 10 |
| 250 | 17 | 70 | 30 | 12 |
| 260 | 25 | 65 | 35 | 16 |
| 280 | 37 | 63 | 32 | 23 |
| 320 | 64 | 55 | 35 | 35 |

EXAMPLE 3

Time on Stream Analysis

Pd/ACC-1(a) catalyst was continuously tested for hydrodechlorination of CFC-12 at 250° C. with a gas hourly space velocity of 4800/h and $H_2$/CFC-12=8. The following table shows the product distribution at different time intervals

TABLE 5

Life study on Pd/ACC-1(a) catalyst; temperature = 250° C.; GHSV = 4800/h; $H_2$/CFC-12 = 8

| Time (hours) | Conversion of CFC-12 | Selectivity for HFC-32 | Methane selectivity |
|---|---|---|---|
| 1 | 81.4 | 85.8 | 11.5 |
| 2 | 80.2 | 86.3 | 11 |
| 3 | 85.4 | 85.5 | 11.6 |
| 4 | 81.5 | 86.6 | 10.6 |
| 5 | 82 | 86.6 | 10.5 |
| 6 | 82.1 | 87 | 10.3 |
| 7 | 81.7 | 87.3 | 10 |
| 8 | 80.6 | 87.5 | 9.8 |
| 9 | 81 | 87.2 | 10 |
| 10 | 82 | 87.4 | 9.8 |
| 11 | 82 | 87.5 | 9.7 |
| 12 | 80.4 | 88 | 9.3 |

We claim:

1. A process for hydrodechlorination of a dichlorodifluoromethane compound comprising:
   placing a carbon supported palladium catalyst in a reactor, and
   feeding a dichlorodifluoromethane compound to the reactor,
   wherein the carbon supported palladium catalyst used is prepared by a process for the synthesis of highly active modified carbon supported palladium catalyst comprising simultaneously impregnating activated carbon with a palladium precursor and an aluminum precursor, wherein the aluminum precursor used comprises an organic precursor of aluminum, and the organic aluminum precursor used comprises aluminum isopropoxide.

2. A process according to claim 1 wherein a resulting product of the process is a difluoromethane compound.

3. A process according to claim 2 wherein the difluoromethane compound is difluoromethane.

4. A process according to claim 1 wherein the dichlorodifluoromethane compound is dichlorodifluoromethane.

5. A process according to claim 1 wherein the palladium precursor used comprises palladium chloride.

6. A process according to claim 1 wherein the palladium loading percentage on the support is in the range of 2–6 wt % with respect to the carbon support.

7. A process according to claim 1 wherein the palladium loading percentage on the support is 4 wt % with respect to the carbon support.

8. A process according to claim 1 wherein a loading percentage of the aluminum precursor in the support is in the range of 1–50 wt % with respect to the support.

9. A process according to claim 1 wherein a loading percentage of the aluminum precursor in the support is in the range of 5–20 wt % with respect to the support.

10. A process according to claim 1 wherein the dichlorodifluoromethane compound is dichlorodifluoromethane and wherein a resulting product of the process is a difluoromethane.

11. A process according to claim 10 wherein said process involves conversion of dichlorodifluoromethane on the order of 85% and selectivity to difluoromethane on the order of 85%.

12. A process according to claim 10 wherein said process involves conversion of dichlorodifluoromethane on the order of 85% and selectivity to difluoromethane on the order of 85% at atmospheric pressure.

13. A process according to claim 10 wherein the catalyst is utilized for hydrodechlorination of dichlorodifluoromethane at a temperature of 250° C.

14. A process according to claim 10 wherein the catalyst is utilized for hydrodechlorination of dichlorodifluoromethane at a temperature of 250° C. and a gas hourly space velocity of 4800/h.

15. A process for hydrodechlorination of a dichlorodifluoromethane compound comprising: placing a carbon supported palladium catalyst in a reactor, and feeding a dichlorodifluoromethane compound to the reactor, and wherein the carbon supported palladium catalyst used is prepared by a process for the synthesis of highly active modified carbon supported palladium catalyst comprising simultaneously impregnating activated carbon with a palladium precursor and an aluminum precursor, wherein the co-impregnation of the support is done in the presence of a tetraethyl ammonium hydroxide aqueous solution, and wherein the aluminum precursor comprises an organic precursor of aluminum and wherein the organic aluminum precursor used comprises aluminum isopropoxide.

16. A process according to claim 15 wherein the aluminum precursor used comprises an organic precursor of aluminum.

17. A process according to claim 16 wherein the organic aluminum precursor used comprises aluminum isopropoxide.

18. A process according to claim 15 wherein the palladium precursor used comprises palladium chloride.

19. A process according to claim 15 wherein the palladium loading percentage on the support is in the range of 2–6 wt % with respect to the carbon support.

20. A process according to claim 15 wherein the palladium loading percentage on the support is 4 wt % with respect to the carbon support.

21. A process according to claim 15 wherein a loading percentage of the aluminum precursor in the support is in the range of 1–50 wt % with respect to the support.

22. A process according to claim 15 wherein a loading percentage of the aluminum precursor in the support is in the range of 5–20 wt % with respect to the support.

23. A process according to claim 15 wherein the dichlorodifluoromethane compound is dichlorodifluoromethane and wherein a resulting product of the process is a difluoromethane.

24. A process according to claim 23 wherein said process involves conversion of dichlorodifluoromethane on the order of 85% and selectivity to difluoromethane on the order of 85%.

25. A process according to claim 23 wherein said process involves conversion of dichlorodifluoromethane on the order of 85% and selectivity to difluoromethane on the order of 85% at atmospheric pressure.

26. A process according to claim 23 wherein the catalyst is utilized for hydrodechlorination of dichlorodifluoromethane at a temperature of 250° C.

27. A process according to claim 23 wherein the catalyst is utilized for hydrodechlorination of dichlorodifluoromethane at a temperature of 250° C. and a gas hourly space velocity of 4800/h.

28. A method for preparing difluoromethane comprising reacting dichlorodifluoromethane with hydrogen in the presence of a carbon supported palladium catalyst, wherein the carbon supported palladium catalyst used is prepared by a process for the synthesis of highly active modified carbon supported palladium catalyst comprising simultaneously impregnating activated carbon with a palladium precursor and an aluminum precursor, wherein the aluminum precursor used comprises an organic precursor of aluminum, and the organic aluminum precursor used comprises aluminum isopropoxide.

29. A method according to claim 28 further comprising the use of an inert gas.

30. A method according to claim 28 wherein the reaction is conducted at a temperature of 200 to 500° C.

31. A method according to claim 28 wherein the reaction is conducted at a temperature of 300 to 400° C.

* * * * *